(12) United States Patent
Ezure

(10) Patent No.: US 11,327,030 B2
(45) Date of Patent: May 10, 2022

(54) METHOD FOR PREPARING SAMPLE FOR X-RAY IMAGING

(71) Applicant: SHISEIDO COMPANY, LTD., Tokyo (JP)

(72) Inventor: Tomonobu Ezure, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 493 days.

(21) Appl. No.: 16/345,652

(22) PCT Filed: Oct. 26, 2017

(86) PCT No.: PCT/JP2017/038794
§ 371 (c)(1),
(2) Date: Apr. 26, 2019

(87) PCT Pub. No.: WO2018/079682
PCT Pub. Date: May 3, 2018

(65) Prior Publication Data
US 2020/0057007 A1   Feb. 20, 2020

(30) Foreign Application Priority Data
Oct. 28, 2016   (JP) .............................. JP2016-212330

(51) Int. Cl.
*G01N 23/046*   (2018.01)
*G01N 1/30*   (2006.01)
*G01N 33/483*   (2006.01)

(52) U.S. Cl.
CPC ............. *G01N 23/046* (2013.01); *G01N 1/30* (2013.01); *G01N 33/4833* (2013.01); *G01N 2001/302* (2013.01)

(58) Field of Classification Search
CPC .................................................. G01N 33/4833
See application file for complete search history.

(56) References Cited

FOREIGN PATENT DOCUMENTS

WO   WO-2015/188040 A2   12/2015

OTHER PUBLICATIONS

Prabhu et al., Clinical Dermatology, 2007, 33:262-265.*
Walton et al., Sci. Rep., 2015, 5, 10074, pp. 1-14 as printed.*
Pauwels et al., "An exploratory study of contrast agents for soft tissue visualization by means of high resolution X-ray computed tomography imaging," Journal of Microscopy, Apr. 22, 2013, 250(Pt. 1):21-31.
Rissmann et al., "Skin barrier disruption by acetone: observations in a hairless mouse skin model," Arch. Dermatol. Res., Apr. 7, 2009, 301:609-613.
Shearer et al., "Three-dimensional visualization of soft biological structures by X-ray computed micro-tomography," Journal of Cell Science, 2016, 129:2483-2492.

* cited by examiner

*Primary Examiner* — Bin Shen
(74) *Attorney, Agent, or Firm* — Foley & Lardner LLP

(57) ABSTRACT

The present invention addresses the problem of providing a method for observing skin tissue in which x-ray microCT is used. Adnexae such as sweat glands, sebaceous glands, and hair follicles can be identified in skin tissue by using acetone as a pretreatment solution and staining using an iodine-containing solution as a staining solution.

20 Claims, 5 Drawing Sheets

FIG. 3
(A)
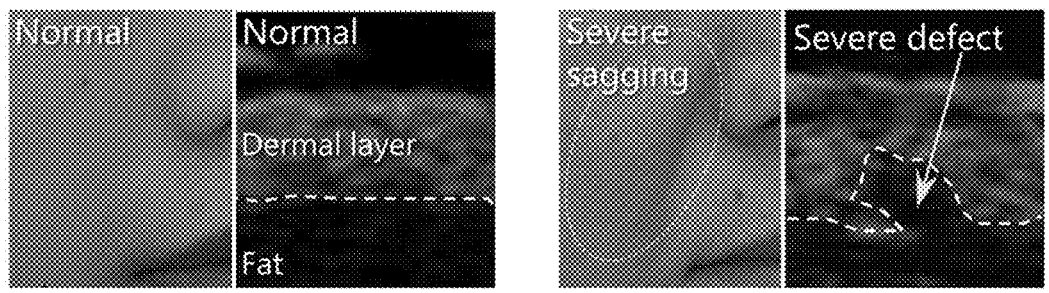
(B)
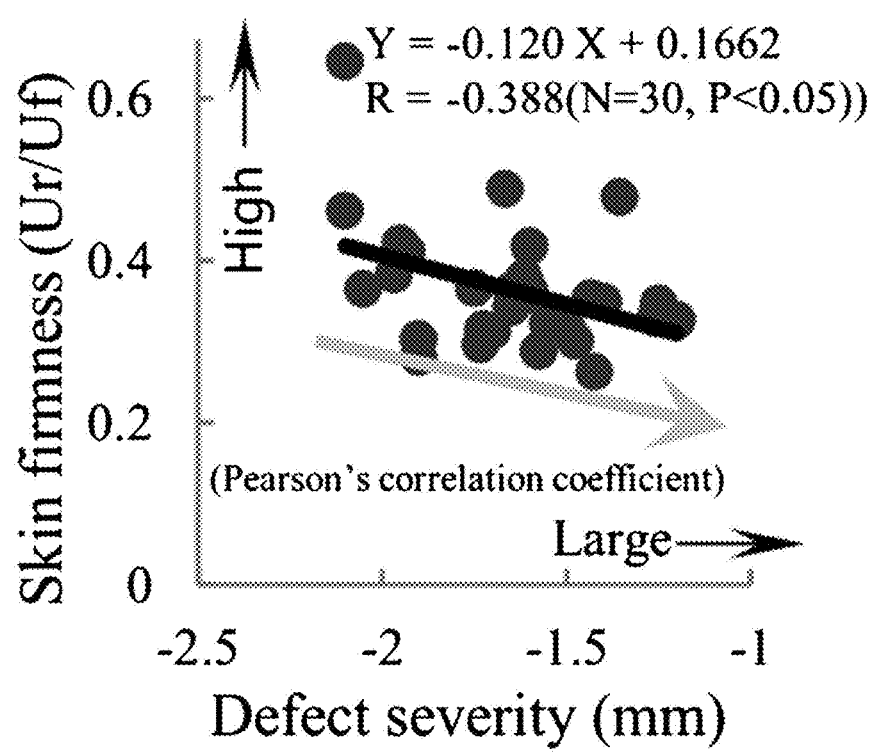

METHOD FOR PREPARING SAMPLE FOR X-RAY IMAGING

CROSS-REFERENCE TO RELATED APPLICATIONS

This application is the U.S. National Stage of PCT/JP2017/038794, filed Oct. 26, 2017, which claims priority to JP 2016-212330, filed Oct. 28, 2016.

FIELD

The present invention relates to the technical field of X-ray imaging method of skin samples.

BACKGROUND

X-rays are highly penetrative but the penetration thereof differs depending on the materials. Thys, X-rays are utilized in the fields of medicine and non-destructive internal inspection by using this difference in penetration. Technology for obtaining 3-dimensional images by processing X-ray images with a computer has been developed and is referred to as computed tomography (CT). If the effects of exposure to radiation are not taken into account, CT allows for extremely high resolution such that 3-dimensional images of fine structures at a microscopic level or greater can be obtained. This type of CT is referred to as X-ray micro-CT. Although the application thereof on living bodies is not desirable, this technique is suitable for observing the obtained 3-dimensional structure within tissue in more detail.

Since the development of X-ray micro-CT, X-ray micro-CT has been making it possible to acquire and analyze cross-sectional images of various substances including isolated tissue, molded resin products, and small electronic components.

CITATION LIST

Patent Literature

[NPL 1] Journal of Cell Science (2016), vol. 129, pp, 2483-2492

SUMMARY

Technical Problem

The inventors of the present invention has attempted to analyze the 3-dimensional structure of skin from a human skin tissue sample by using X-ray micro-CT. While X-ray micro-CT has made it possible to distinguish the rough structural differences of the epidermis, dermis, and subcutaneous fat layers, it has not been possible to distinguish the structure of the adnexa contained in the skin structure.

Solution to Problem

Thus, the inventors carried out extensive research on the settings of X-ray micro-CT and preparation of tissue samples. Surprisingly, by pretreating the skin tissue sample with acetone, staining the sample with iodine-containing solution and then loading the sample onto an X-ray micro CT device the adnexa, which are the minute appendages contained in the skin, could be distinguished. Thus, the inventors achieved the present invention.

Specifically, the invention relates to a method of observing a skin sample with an X-ray imaging method. The observation method is characterized by comprising the steps of:

bringing a skin sample into contact with acetone;
bringing the skin sample into contact with an iodine-containing solution; and
obtaining a 3-dimensional image of the skin sample using an X-ray computational tomography apparatus.

In another aspect, the present invention relates to a method of preparing a skin sample for X-ray imaging. The preparation method of the present invention is characterized by comprising the steps of:

bringing a skin sample into contact with an acetone-containing solution; and
bringing the skin sample into contact with an iodine-containing solution.

In yet another aspect, the present invention relates to a method of detecting skin cavitation by measuring the depth of the lowermost part of a sweat gland using the observation method of the present invention.

Advantageous Effects of Invention

By observing skin samples prepared using the skin sample preparation method of the present invention, it is possible to observe the structure of adnexa, which are the minute appendages contained in the skin. Furthermore, by measuring the depth of sweat glands, which are a type of adnexa, skin cavitation can be detected.

BRIEF DESCRIPTION OF DRAWINGS

FIG. 3A shows photographs of the external appearance and ultrasound images of the internal appearance of normal skin and severe sagging skin. The boundary between the dermal layer and the subcutaneous fat is flat in normal skin whereas in severe sagging skin severe defects can be seen. FIG. 3B is a graph illustrating the relationship between the defect severity and skin firmness of dermal cavities. The larger the dermal cavity, the lower the skin firmness, and the smaller the dermal cavity the higher the firmness. The correlation coefficient is the Pearson's correlation coefficient.

DESCRIPTION OF EMBODIMENTS

Figure 1:
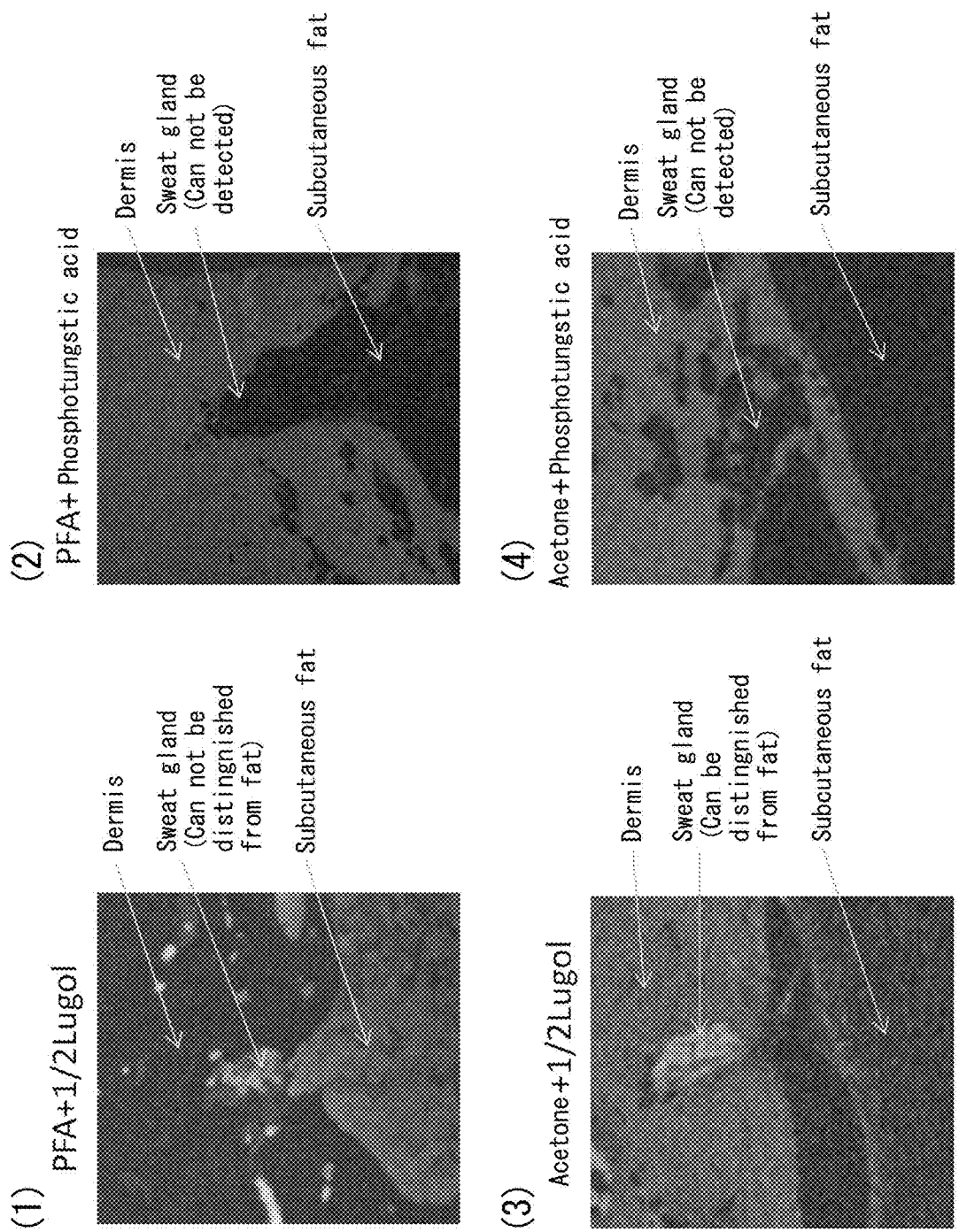
FIG. 1 shows 3-dimensional images obtained by X-ray micro-CT wherein treatment was carried out using, as a combination of a pretreatment solution and a staining solution, (1) PFA and an iodine-containing solution (Lugol), (2) PFA and phosphotungstic acid, (3) acetone and an iodine-containing solution (Lugol), and (4) acetone and phosphotungstic acid.

The present invention relates to a method of observing a skin sample with an X-ray imaging method. The observation method is characterized by comprising the steps of:

bringing a skin sample into contact with an acetone-containing solution;

bringing the skin sample into contact with an iodine-containing solution; and obtaining a 3-dimensional image using an X-ray computational tomography apparatus.

An appropriate output and resolution can be selected for the X-ray imaging method. As 3-dimensional structures are to be observed, tomography (CT imaging) is preferable. Furthermore, in view of observing minute appendages such as adnexa, an imaging method that has a resolution of 0.1 μm or less, the imaging method referred to as X-ray micro-CT is preferable. In view of observing smaller tissues, the resolution of the X-ray micro-CT is preferably 0.1 μm or less, more preferably 0.01 μm or less, and even more preferably 0.05 μm or less. Although there is no particular lower limit, depending on the capacity of the X-ray CT apparatus, the resolution is, for example, 0.0001 μm or more, or 0.001 μm or more.

The skin sample is a sample obtained from the skin. The skin sample is acceptable provided the form obtained includes the region intended to be observed. The skin sample is acceptable provided at least one from the epidermis, dermis, and subcutaneous tissue is included. Skin sections may be used or 3-dimensional cultured skin models may be used. The animal from which the skin sample originates is not limited but examples thereof include humans, pigs, cattle, mice, rats, rabbits, horses, etc. In particular, human skin is preferable but the skin of pigs which have a structure resembling human skin is also preferable as the observation material.

The epidermis is the outermost layer of skin that exists in the skin tissue. The epidermis is mainly composed of the horny layer, the granular layer, the spinous layer and the basal layer. The basal cells present in the basal layer divide and migrate to the outer layer, differentiating into the cells of the horny layer through denuclearization and flattening during the migration process, and are ultimately peeled off. In addition to keratinocytes, cells such as melanocytes, Langerhans cells and Merkel cells exist in the epidermis. The basement membrane exists at the boundary between the epidermis and the dermis and is raised to form a papilla structure. The dermis is composed of the papillary layer, the subpapillary layer, and the reticular layer. The hair apparatus and secretory glands such as sweat glands and sebaceous glands are present in the form of depressions through the epidermis and dermis. Secretory glands include eccrine sweat glands, apocrine sweat glands, sebaceous glands, and pilosebaceous glands. The hair apparatus includes the hair follicle, hair, and arrector pili muscle. Of the secretory glands, apocrine sweat glands and pilosebaceous glands are associated with the hair apparatus. It was difficult to distinguish the hair apparatus or secretory glands with conventional X-ray micro-CT. However, when the sample was prepared by the preparation method and observed by the observation method of the present invention, it was possible to distinguish such adnexa.

The acquired skin sample may be stored in a refrigerated or frozen state after acquisition or may be brought into contact with an acetone-containing solution immediately after acquisition. Any solution may be used as the acetone-containing solution, provided that the solution contains acetone. The amount of acetone is preferably 50% or more, more preferably 80% or more, and most preferably 100% acetone.

The contact time with the acetone-containing solution can be appropriately selected according to the size of the skin sample. For example, for a skin section with a 5 mm thickness the contact time can be 6 hours or more, preferably 12 hours or more, and more preferably 24 hours or more. There is no particular upper limit to the contact time but in view of simplifying the experiment the contact time is 48 hours less, more preferably 24 hours or less. The step of bringing an acetone-containing solution into contact with the sample may be carried out at any temperature, for example, at room temperature or under refrigeration. In view of handling a biological sample, it is preferable for the step to be carried out under refrigeration, for example 4° C.

In the present invention, any solution is acceptable for the iodine-containing solution provided that iodine or iodide is included. As iodine has a high X-ray absorption rate, it is considered that it will be possible to distinguish tissue by X-ray imaging according to the degree of deposition of iodine. Thus, the iodine-containing liquid can be referred to as a staining solution. Iodide can be used to assist the dissolution of iodine. The iodide contained in the iodine-containing solution of the present invention may be any iodide, for example, hydrogen iodide, sodium iodide, potassium iodide, and carbon tetraiodide. A mixed solution of iodine and potassium iodide may be used and, for example, Lugol's solution may be used. An iodine-containing solution with a total iodide and iodine concentration of 0.1 to 10%, and more preferably 1 to 5% can be used. The mixing ratio of iodide and iodine can be appropriately selected from between 1:10 to 10:1. The mixing ratio is preferably 1:5 to 5:1 and more preferably 1:2 to 2:1. In Lugol's solution, potassium iodide and iodine exist at a ratio of 2:1 and are used at a total amount of 3.75%.

The contact time with the iodine-containing solution can be appropriately selected according to the size of the skin sample. For example, for a skin section with a thickness of 5 mm, the contact time can be 12 hours or more, preferably 24 hours or more, and more preferably 48 hours or more. There is no particular upper limit to the contact time but in view of simplifying the experiment the contact time is 96 hours or less and more preferably 48 hours or less. The step of bringing an acetone-containing solution into contact with the sample may be carried out at any temperature, for example, at room temperature or under refrigeration. However, in view of handling a biological sample, it is preferable for the step to be carried out under refrigeration, for example 4° C.

In the present invention, a washing step for rinsing off the solutions used in each step may be carried out before or after each step. The washing step is carried out by substituting the solution being used with an appropriate solution one to multiple times. In view of handling biological samples, phosphate buffered saline (PBS) may be used as the solution, or the solution used in the following step may also be used as the solution.

After the step of bringing the sample into contact with an iodine-containing solution, imaging is carried out with an X-ray computational tomography apparatus to acquire 3-dimensional images. Imaging may be carried out by selecting an appropriate output for an X-ray CT apparatus. In view of increasing the resolution, imaging can be performed with an output of preferably 10 kV or more, more preferably 25 kV, and preferably 100 kV or less, more preferably 50 kV or less. As one example, observations can be carried out by setting μCT apparatus (D200RSS270) manufactured by Comscan Techno to an output of 50 kV and an X-ray tube current of 200 μA.

Figure 4:
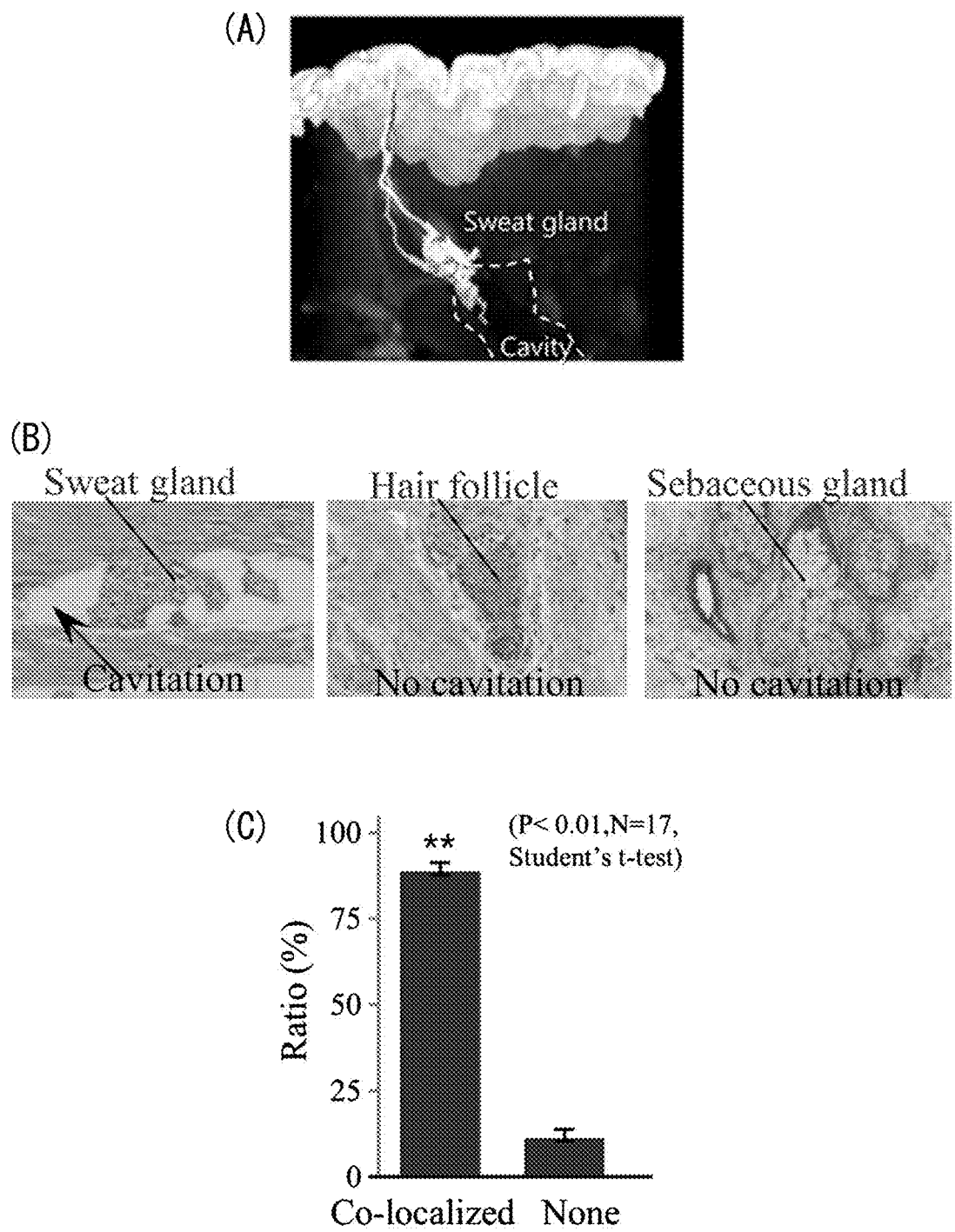
FIG. 4A shows a 3-dimensional image of a part including a sweat gland obtained by X-ray micro-CT. A cavity can be seen on the lower side of the sweat gland.
FIG. 4B shows photographs of stained tissue sections of a sweat gland, hair follicle, and sebaceous gland. There was cavitation in the sweat gland but there was no cavitation in the hair follicle and sebaceous gland.
FIG. 4C is a graph showing the ratio of colocalization of sweat glands and dermal cavities. There was no colocalization (none) for approximately 10%. Significant differences were obtained by student's t-test.

When the skin sample was made visible by the X-ray micro-CT using the method of the present invention, sweat glands with a shrunken length from the surface of the skin were discovered. Such sweat glands will be referred to as shrunken sweat glands. Among the sweat glands, eccrine sweat glands in particular were shrunken. Shrunken sweat glands were often observed mainly in the skin of the elderly. The lowermost part of the sweat gland usually exists at the boundary between the dermis and the subcutaneous tissue. Thus, shrunken sweat glands move to the side of the skin surface layer just for the shrunken portion, and the region through which shrunken sweat glands move was replaced with subcutaneous tissue (FIGS. 3 and 4). Cavities formed by such subcutaneous tissue raised towards the dermis will be referred to as dermal cavities. The dermal cavities are approximately spherical have a diameter of about 10 μm to 1000 μm, but the shape is not fixed and. As the interior was filled with subcutaneous fat tissue the dermal cavities could simply be referred to as dermal recesses. Cellular components and interstitial components contained in the dermis layer are not included in the dermal cavities and so skin firmness is lost, sagging occurs and skin aging is thought to be linked thereto (PCT/JP2015/072140).

Thus, sagging of the skin can be measured by assessing whether sweat glands have shrunken. Shrink of sweat glands can be determined based on the depth of the lowermost part of the sweat gland from the skin surface. Shrinkage can also be determined from the distance ($L_1$) from the skin surface to the subcutaneous fat tissue in a region where there are no sweat glands and where the subcutaneous fat tissue is not raised, and the distance ($L_2$) from the skin surface to the lowermost part of a sweat gland (or to the subcutaneous tissue) in a region where there are sweat glands by, for example, with the following formula.

Degree of sweat gland shrinkage=$L_1-L_2/L_1$ [Formula 1]

As the depth increases the degree of atrophication decreases and cavitation of the skin decreases. On the other hand, as the depth decreases shrinkage increases and cavitation of the skin increases.

Thus, by measuring the degree of shrinkage of sweat glands using the observation method of the present invention, skin cavitation can be detected.

All references mentioned herein are incorporated by reference in their entirety.

The embodiments of the present invention described below are merely for illustrative purposes and do not limit the technical scope of the present invention. Only the claims limit the technical scope of the present invention. On the condition that there is no deviation from the purpose of the present invention, changes such as the addition, removal, or substitution of constituent elements of the present invention can be carried out.

EXAMPLES

Example 1

A skin sample was pretreated with 4% PFA or acetone, soaked in Lugol or phosphotungstic acid and washed with PBS, and was thereafter imaged by CT.

Skin samples were obtained from surplus skin of 17 female subjects and 20 male subjects who had undergone plastic surgery and cut to a thickness of 5 mm. Pretreatment was carried out by washing with PBS, then putting the skin samples in acetone and leaving for 24 hours at 4° C. in an incubator. For comparison, a 4% aqueous PFA solution was used instead of the acetone for pretreatment. After incubating, the skin sample was washed with PBS. Next, the skin sample was put into an iodine-containing solution (2.5% potassium iodide and 1.25% iodine solution) which was obtained by diluting a diluted Lugol's solution and incubated for 24 hours at 4° C. As a comparison, instead of the iodine-containing solution, a phosphotungstic acid solution was used. The phosphotungstic acid-containing solution was made from a stock solution containing 6.7% phosphotungstic acid, by adding 1.5 ml of water and 7 ml of 100% ethanol to 1.5 ml of the stock solution, and was used as a stain solution, and then the sample was stained therewith. After staining, the sample was washed with PBS and then measured by μCT (D200RSS, Comscan Techno). FIG. 1 shows images obtained by X-ray micro-CT using the following combinations of a pretreatment solution/a staining solution: (1) PFA/iodine-containing solution (Lugol); (2) PFA/phosphotungstic acid; (3) acetone/iodine-containing solution (Lugol); and (4) acetone/phosphotungstic acid.

Figure 2:
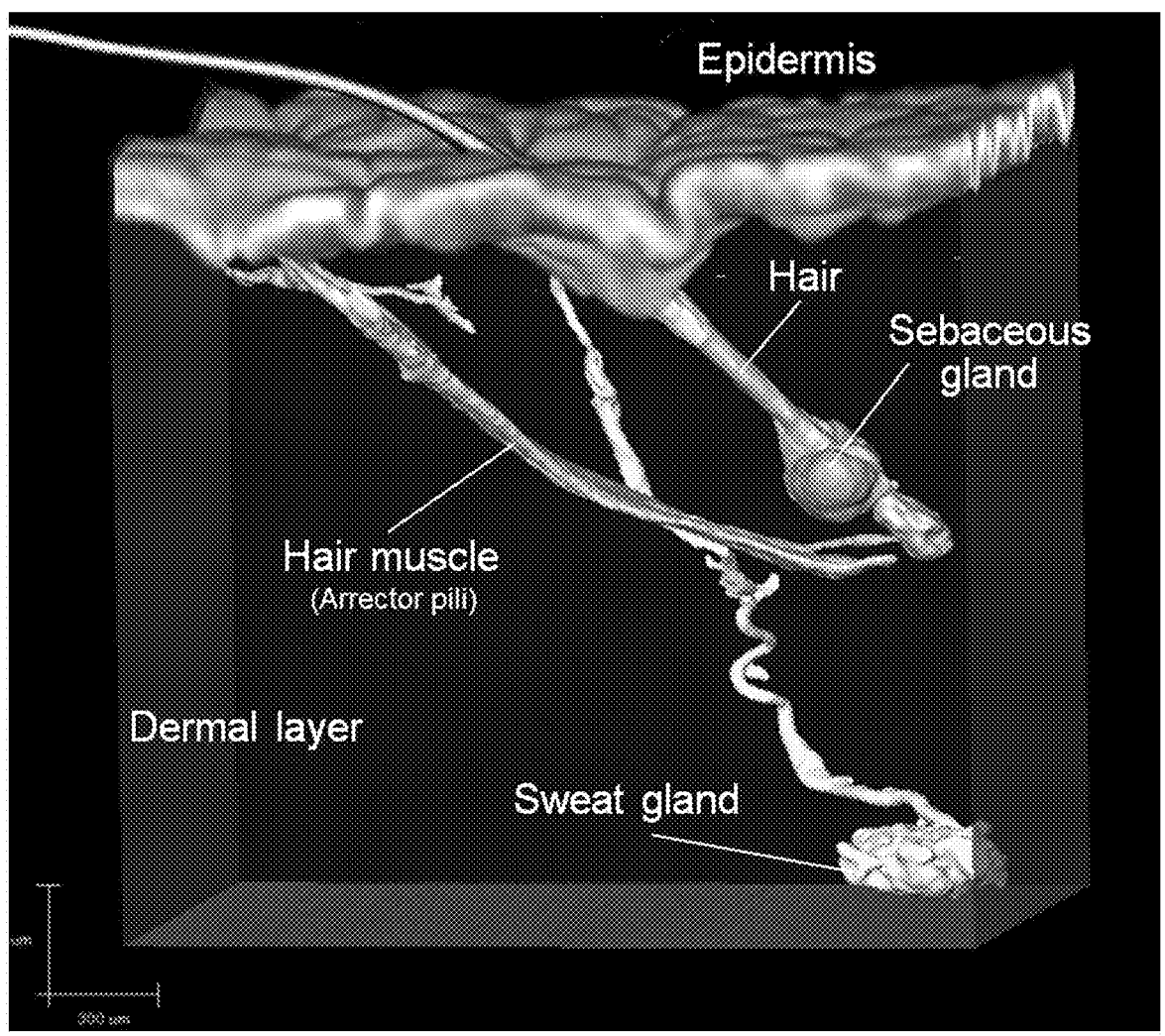
FIG. 2 is a 3-dimensional image obtained by X-ray micro-CT in which a sample was treated using a combination of acetone and an iodine-containing solution and illustrates the hair apparatus (hair, hair muscle (arrector pili), sweat gland, and sebaceous gland) together with the tissue (epidermis and dermal layer).

FIG. 2 shows a 3-dimensional image using (3) acetone/iodine-containing solution as the pretreatment/staining solution. FIG. 2 shows the hair apparatus (hair, hair muscle, arrector pili, sweat gland, and sebaceous gland) in addition to the tissue (epidermis and dermal layer).

Example 2

Photographs were taken of the outward appearance of the skin of two women of the same age in their thirties then internal images of the skin were acquired with an ultrasound imaging apparatus. The outward appearance of the skin was normal for one woman but sagging for the other. FIG. 3A shows the outward appearance and ultrasound images of the skin. Even in subjects of the same age, in the subject with sagging skin, ridges in the fat tissue towards the dermal part (hereinafter referred to as dermal cavities) could be seen in the ultrasound images whereas in subjects with non-sagging normal skin such cavities could not be observed. Next, the size of dermal cavities in the skin and the consistency thereof were measured for different subjects. Skin firmness was determined by measuring the Ur/Uf value with a cutometer. The results are shown in 3B.

In order to determine the cause of the dermal cavities, the inventors of the present invention analyzed the 3-dimensional images obtained in EXAMPLE 1 and discovered that sweat glands were present in the location where the dermal cavities were present (FIG. 4A). In order to examine the relationship between sweat glands and dermal cavities, sweat glands, sebaceous glands, and hair follicles were observed in images of stained tissue section and it was found that dermal cavities exist specifically in sweat glands (FIG. 4B). The colocalization rate of sweat glands and dermal cavities was calculated (FIG. 4C).

Figure 5:
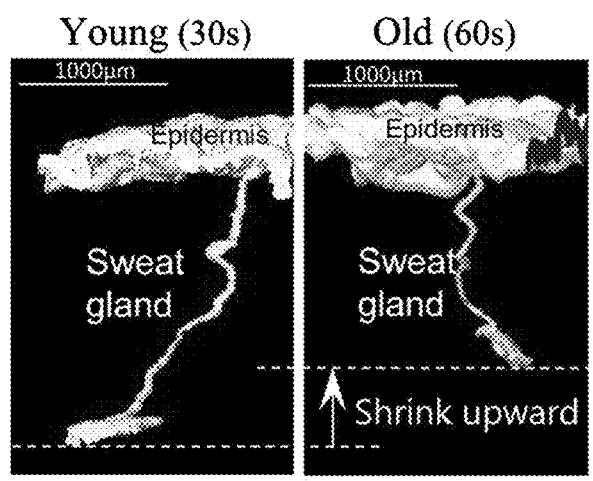
FIG. 5 shows 3-dimensional images of sweat gland portions of the skin of a young subject in their 30s and an old subject in their 60s. In the skin of the old subject, the sweat gland shrank upward in the direction to the epidermis side.

Next, comparing the sweat glands of skin of subjects in their thirties with the sweat glands of skin of subjects in their sixties both in 3-dimensional images and images of stained tissue sections, it was found that the position of sweat glands in the skin of subjects in their sixties were shallow and that shrinkage is occurred accompanying with aging (FIG. 5).

Furthermore, it was found that in the region in which sweat glands had shrunken, the fat tissue was raised to form a dermal cavity.

The depth of sweat glands in the skin were determined for subjects in their thirties and subjects in their sixties. The depths were represented by the distance from the surface of the skin to the lowermost part of the sweat gland. The severity of dermal cavitation was represented by the distance from the surface of the skin to the uppermost part of the cavity. Thus, the correlation between sweat gland depth and age, and sweat gland depth and the severity of dermal cavitation was examined. The results are shown in the table below.

TABLE 1

|  | Sweat gland depth | |
| --- | --- | --- |
|  | R | P value |
| Age | 0.699 | <0.001 |
| Severity of dermal cavitation | 0.854 | <0.001 |

The invention claimed is:

1. An observation method of a skin sample by an X-ray imaging method, comprising the steps of:
   bringing a skin sample into contact with an acetone-containing solution;
   then bringing the skin sample into contact with an iodine-containing solution; and
   obtaining a 3-dimensional image of the skin sample using an X-ray computational tomography apparatus.

2. The observation method of claim 1, wherein the method comprises displaying adnexa in the obtained 3-dimensional image of the skin sample.

3. The observation method of claim 2, wherein the adnexa is selected from the group consisting of sebaceous glands, sweat glands, and hair apparatus.

4. The observation method of claim 3, wherein the iodine-containing solution contains at least one of potassium iodide and iodine.

5. The observation method of claim 1, wherein the iodine-containing solution contains at least one of potassium iodide and iodine.

6. The observation method of claim 2, wherein the iodine-containing solution contains at least one of potassium iodide and iodine.

7. The method of claim 6, wherein the iodine-containing solution contains potassium iodide and iodine.

8. The method of claim 7, wherein a mixing ratio between potassium iodide and iodine in the iodine containing solution is from 1:5 to 5:1.

9. The method of claim 1, wherein the acetone-containing solution containing at least 80% or more of acetone.

10. A method for preparing a skin sample for X-ray imaging, comprising the steps of:
    bringing a skin sample into contact with an acetone-containing solution;
    then bringing the skin sample into contact with an iodine-containing solution; and
    X-ray imaging the skin sample.

11. The preparation method of claim 10 wherein the iodine-containing solution contains at least one of potassium iodide and iodine.

12. The method of claim 11, wherein the iodine-containing solution contains potassium iodide and iodine.

13. The method of claim 12, wherein a mixing ratio between potassium iodide and iodine in the iodine containing solution is from 1:5 to 5:1.

14. The method of claim 10, wherein the acetone-containing solution containing at least 80% or more of acetone.

15. A method of detecting skin cavitation comprising
    bringing a skin sample into contact with an acetone-containing solution;
    then bringing the skin sample into contact with an iodine-containing solution;
    obtaining a 3-dimensional image of the skin sample using an X-ray computational tomography apparatus;
    measuring a depth of adnexa in the obtained 3-dimensional image of the skin sample to detect cavitation in the skin sample.

16. The method of claim 15, wherein the adnexa is selected from the group consisting of sebaceous glands, sweat glands, and hair apparatus.

17. The method of claim 15, wherein the iodine-containing solution contains at least one of potassium iodide and iodine.

18. The method of claim 17, wherein the iodine-containing solution contains potassium iodide and iodine.

19. The method of claim 18, wherein a mixing ratio between potassium iodide and iodine in the iodine containing solution is from 1:5 to 5:1.

20. The method of claim 15, wherein the acetone-containing solution containing at least 80% or more of acetone.

* * * * *